US008697626B2

(12) United States Patent
Moretti

(10) Patent No.: US 8,697,626 B2
(45) Date of Patent: Apr. 15, 2014

(54) 4,4-DIMETHYL-DECAL-1-ONE OR -1-OL DERIVATIVES AS PERFUMING INGREDIENTS

(75) Inventor: Robert Moretti, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/825,316

(22) PCT Filed: Sep. 27, 2011

(86) PCT No.: PCT/EP2011/066706
§ 371 (c)(1),
(2), (4) Date: Mar. 20, 2013

(87) PCT Pub. No.: WO2012/041820
PCT Pub. Date: Apr. 5, 2012

(65) Prior Publication Data

US 2013/0190218 A1 Jul. 25, 2013

(30) Foreign Application Priority Data

Oct. 1, 2010 (EP) .................................... 10185744

(51) Int. Cl.
*A61K 8/00* (2006.01)

(52) U.S. Cl.
USPC ............................................................ 512/15

(58) Field of Classification Search
USPC ............................................................ 512/15
See application file for complete search history.

(56) References Cited

FOREIGN PATENT DOCUMENTS

| | | | |
|---|---|---|---|
| EP | 0 167 709 | A2 | 1/1986 |
| EP | 1 605 035 | A1 | 12/2005 |
| WO | WO 2007/031904 | A1 | 3/2007 |
| WO | WO 2009/044310 | A1 | 4/2009 |

OTHER PUBLICATIONS

H. Liu et al., Canadian Journal of Chemistry 1987, vol. 65, pp. 182-188.*
E.C. Angell et al., Journal of Organic Chemistry 1986, vol. 51, pp. 5177-5182.*
A. Bannerjee et al., Recueil des Travaux Chimiques des Pays-Bas 1995, vol. 114, pp. 87-90.*
W.A. Donaldson et al., Organic Preparations and Procedures International 1989, vol. 21, pp. 219-221.*
International Search Report and Written Opinion, application No. PCT/EP2011/066706, mailed Feb. 6, 2012.
Cook et al, J. Chem. Soc., Perkin Transactions 1:529-537 (1973).

* cited by examiner

*Primary Examiner* — John Hardee
(74) *Attorney, Agent, or Firm* — Winston & Strawn LLP

(57) ABSTRACT

The present invention relates to use of a compound of formula (I) in the form of any one of its stereoisomers or a mixture thereof, and wherein the dotted lines represent a single or double bond, and at least one of said dotted lines represents a double bond; n represents simultaneously 0, in which case the oxygen atom is bounded to the cyclanic carbon atom by a double bond, or 1, in which case the oxygen atom is bounded to the cyclanic carbon atom by a single bond, each R represents a hydrogen atom or a methyl group; $R^1$ represents a hydrogen atom or a methyl or ethyl group; and $R^2$ represents a hydrogen atom or a methyl or ethyl group; and the groups R, $R^1$ and $R^2$ have in total, i.e. all together account for 1 to 4 carbon atoms; as perfuming ingredient, for instance to impart odor notes of the woody type together with balsamic/spicy and/or musky notes.

(I)

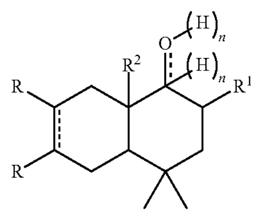

16 Claims, No Drawings

4,4-DIMETHYL-DECAL-1-ONE OR -1-OL DERIVATIVES AS PERFUMING INGREDIENTS

TECHNICAL FIELD

The present invention relates to the field of perfumery. More particularly, it concerns the use as perfuming ingredient of a 4,4-dimethyl-decal-1-one or -1-ol as defined herein below. Moreover the present invention comprises the invention's compound as part of a perfuming composition or of a perfuming consumer product.

PRIOR ART

To the best of our knowledge, none of the invention's compounds has been reported as having odor properties, and therefore their usefulness as perfuming ingredients is new and non-obvious.

Some structural analogues are known as being useful perfuming ingredients. For instance EP 1605035 reports some compounds, such as 4,6,8a-trimethyl-3,4,4a,5,8,8a-hexahydro-1(2H)-naphthalenone. This compound, as well as all the others reported in EP 1605035, although being the closest analogue known possesses a very different odor character. This document, or the compounds cited therein, does not report or suggest any organoleptic properties of the compounds of formula (I), in particular the presence of spicy notes, nor does it suggest any use of said compounds in the field of perfumery.

DESCRIPTION OF THE INVENTION

We have now surprisingly discovered that a compound of formula (I)

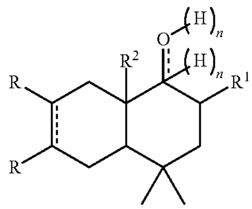

in the form of any one of its stereoisomers or a mixture thereof, and wherein the dotted lines represent a single or double bond, and at least one of said dotted lines represents a double bond;

n represents simultaneously 0, in which case the oxygen atom is bounded to the cyclanic carbon atom by a double bond, or 1, in which case the oxygen atom is bounded to the cyclanic carbon atom by a single bond, each R represents a hydrogen atom or a methyl group;

$R^1$ represents a hydrogen atom or a methyl or ethyl group; and $R^2$ represents a hydrogen atom or a methyl or ethyl group;

and the groups R, $R^1$ and $R^2$ have in total, i.e. all together account for, 1 to 4 carbon atoms;

can be used as perfuming ingredient, for instance to impart odor notes of the woody type together with balsamic/spicy and/or musky notes.

According to a particular embodiment of the invention, the compounds of formula (I) are those wherein one R represents a hydrogen atom and the other R represents a hydrogen atom or a methyl group.

According to a particular embodiment of the invention, the compounds of formula (I) are of formula (II)

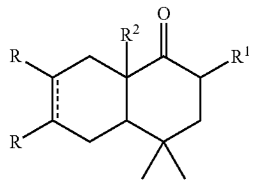

wherein the dotted line represents a single or double bond;

one R represents a hydrogen atom and the other R represents a methyl group or a methyl group;

$R^1$ represents a hydrogen atom or an ethyl group;

$R^2$ represents a hydrogen atom or a methyl or ethyl group; and the groups R, $R^1$ and $R^2$ have in total, i.e. all together account for, 2 to 3 carbon atoms.

According to a particular aspect of formula (II), the dotted line represents a carbon-carbon double bond.

According to any one of the particular aspects of formula (II), $R^1$ represents a hydrogen atom or an ethyl group.

According to any one of the particular aspects of formula (II), $R^2$ represents a hydrogen atom or a methyl group.

According to any one of the particular aspects of formula (I) or (II), $R^2$ and $R^1$ do not represent simultaneously a hydrogen atom, in particular one of said $R^2$ and $R^1$ represents a hydrogen atom and the other represents an alkyl group as respectively defined.

According to any one of the above embodiments of the invention, said compounds (I) are $C_{14}$-$C_{15}$ compounds.

For the sake of clarity, by the expression "the dotted lines represent a single or double bond", or the similar, it is meant the normal meaning understood by a person skilled in the art, i.e. that the whole bonding (solid and dotted lines) between the carbon atoms, or carbon and oxygen atoms, connected by said dotted line is a single or double bond.

As specific examples of the invention's compounds, one may cite, as non-limiting example, the isomers (4aRS,8aRS)-4,4,6,8a-tetramethyl-3,4,4a,5,8,8a-hexahydro-naphthalen-1(2H)-one or (4aRS,8aRS)-4,4,7,8a-tetramethyl-3,4,4a,5,8,8a-hexahydro-naphthalen-1(2H)-one, as well as the mixtures thereof, which have an odor with woody, rooty, balsamic-liquorice notes and an excellent spicy note. The association of woody notes with the spicy note, reminiscent of pepper and wasabi, is of particular interest for the person skilled in the art. These compounds display also a musky bottom note.

As mentioned above, (4aRS,8aRS)-4,4,6,8a-tetramethyl-3,4,4a,5,8,8a-hexahydronaphthalen-1(2H)-one or (4aRS,8aRS)-4,4,7,8a-tetramethyl-3,4,4a,5,8,8a-hexahydronaphthalen-1(2H)-one can be advantageously used in the form of a mixture thereof. In particular said mixture may contain more than 50% w/w, or even more than 60%, of the (4aRS,8aRS)-4,4,6,8a-tetramethyl-3,4,4a,5,8,8a-hexahydronaphthalen-1(2H)-one isomer.

As other specific, but non-limiting, examples of the invention's compounds, one may cite the following ones in Table 1:

TABLE 1

| Invention's compounds and their odor properties | |
|---|---|
| Structure | Odor |
| 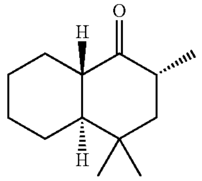<br>(2RS,4aSR,8aSR)-2,4,4-trimethyloctahydronaphthalen-1(2H)-one | Woody, pineol, minty, saffron |
| 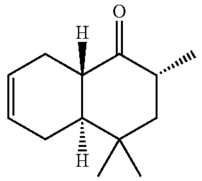<br>(4aRS,8aSR)-2,4,4-trimethyl-3,3,4a,5,8,8a-hexahydronaphthalen-1(2H)-one | Woody, earthy, tonalide |
| 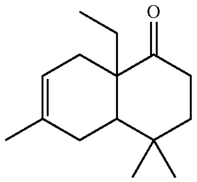<br>8a-ethyl-4,4,6-trimethyl-3,4,4a,5,8,8a-hexahydronaphthalen-1(2H)-one | Woody, glycomel, spicy, cashmeran |
| 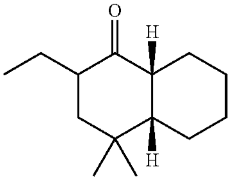<br>(4aRS,8aSR)-2-ethyl-4,4-dimethyloctahydronaphthalen-1(2H)-one | Woody, ambery, nutmeg, balsamic |
| 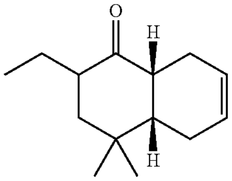<br>(4aRS,8aSR)-2-ethyl-4,4-dimethyl-3,4,4a,5,8,8a-hexahydronaphthalen-1(2H)-one | Woody, animal, balsamic spicy, laurel and slightly cigar box |

TABLE 1-continued

| Invention's compounds and their odor properties | |
|---|---|
| Structure | Odor |
| 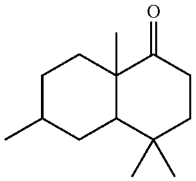<br>4,4,6,8a-tetramethyloctahydro-1(2H)-naphthalenone | Woody, peppery, spicy |
| 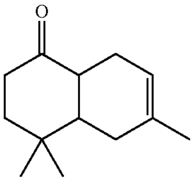<br>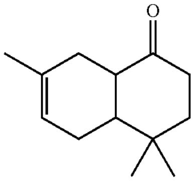<br>mixture of 4,4,6-trimethyl-3,4,4a,6,8,8a-hexahydro-1(2H)-naphthalenone (a) and 3,4,4a,5,8,8a-hexahydro-4,4,6(7)-trimethyl-1(2H)-naphthalenone | Woody, incense, balsamic |
| 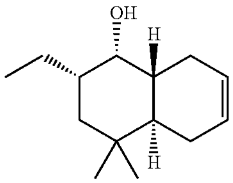<br>(1RS,2RS,4aSR,8aSR)-2-ethyl-4,4-dimethyl-1,2,3,4,4a,5,8,8a-octahydronaphthalen-1-ol | Woody, cypress, spicy, aromatic |

According to a particular embodiment of the invention, the compounds of formula (I) are (4aRS,8aRS)-4,4,6,8a-tetramethyl-3,4,4a,5,8,8a-hexahydronaphthalen-1(2H)-one or (4aRS,8aRS)-4,4,7,8a-tetramethyl-3,4,4a,5,8,8a-hexahydronaphthalen-1(2H)-one and mixtures thereof, 8a-ethyl-4,4,6-trimethyl-3,4,4 a,5,8,8a-hexahydronaphthalen-1(2H)-one, dimethyloctahydronaphthalen-1(2H)-one, or (4aRS,8aSR)-2-ethyl-4,4-dimethyl-3,4,4a,5,8,8a-hexahydronaphthalen-1(2H)-one. According to a particular embodiment of the invention, the compounds of formula (I) are (4aRS,8aRS)-4,4,6,8a-tetramethyl-3,4,4a,5,8,8a-hexahydronaphthalen-1(2H)-one or (4aRS,8aRS)-4,4,7,8a-tetramethyl-3,4,4a,5,8,8a-hexahydronaphthalen-1(2H)-one and mixtures thereof.

When the odor of the invention's compounds is compared with that of the prior art cited above, and in particular 4,6,8a-trimethyl-3,4,4a,5,8,8a-hexahydro-1(2H)-naphthalenone, then the invention's compounds distinguish themselves by lacking the citrus or precious wood note so characteristic of the prior art compound(s) and instead having a characteristic balsamic/spicy and/or musky note. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and ii) a perfumery consumer base;

is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 30% by weight, or even more, of the compounds of the invention based on the weight of the composition into which they are incorporated. Concentrations lower than these, such as in the order of 0.01% to 10% by weight, can be used when these compounds are incorporated into perfumed articles, percentage being relative to the weight of the article.

The invention's compounds can be prepared according to a method as described in the examples herein below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of a mixture of (4aRS,8aRS)-4,4,6,8a-tetramethyl-3,4,4a,5,8,8a-hexahydronaphthalen-1(2H)-one and (4aRS,8aRS)-4,4,7,8a-tetramethyl-3,4,4a,5,8,8a-hexahydronaphthalen-1(2H)-one A 100 ml 3-neck flask equipped with a thermometer, magnetic stir bar was charged with 1.98 g of $AlCl_3$ (14.9 mmol), 3.0 g of Primol (20% w/w) at room temperature. 13.7 g of 2-methyl-cyclohex-2-enone was slowly added and the entire mixture was stirred at 25° C. for 48 hours. The reaction mixture was quenched with a saturated solution of $NaHCO_3$ and the aqueous phase extracted twice with diethyl ether. The organic phases were washed with an aqueous saturated solution of sodium carbonate, with brine and were dried over magnesium sulfate. After filtration and removal of organic solvent under reduced pressure, the obtained crude product was distilled under vacuum and gave 12.0 g of a 7/3 mixture (by GC) of (4aRS,8aRS)-4,4,6,8a-tetramethyl-3,4,4a,5,8,8a-hexahydronaphthalen-1(2H)-one and (4aRS,8aRS)-4,4,7,8a-tetramethyl-3,4,4a,5,8,8a-hexahydronaphthalen-1(2H)-one.

$^{13}C$-NMR: Isomer (A): 20.9, 23.2, 23.6, 28.0, 32.2, 33.6, 33.9, 34.9, 40.7, 46.4, 48.9, 117.6, 132.1, 216.4.

Isomer (B): 20.9, 23.3, 23.4, 23.7, 32.2, 33.6, 34.9, 37.7, 40.7, 47.4, 47.8, 119.5, 130.0, 215.9.

$^1H$-NMR: 0.97 (t, J=5.8, 8H), 1.11 (m, 4H), 2.08 (m, 2H), 1.63 (m, 10H), 2.19 (m, 6H), 2.79 (d.t., J=14.2, J=5.8, 2H), 5.33 (b.s., 1H), 5.39 (b.s., 0.3H).

Example 2

Synthesis of Compounds of Formula (I)

I) General Procedure for the Diels-Alder Coupling

In a 500 ml reactor were introduced the $AlEtCl_2$, 0.1 g of BHT and $CH_2Cl_2$. Then, under vigorous stirring, was added the appropriate cyclohexenone drop wise, so as to maintain the temperature below 30° C. Afterward, was added the diene drop wise and when the reaction ended, the reaction mixture was hydrolyzed with 5% aqueous HCl, extracted twice with $Et_2O$. The organic layer was then washed with a saturated $NaHCO_3$ aqueous solution, water, and brine and then dried over $Na_2SO_4$. Evaporation of the solvents, chromatography ($SiO_2$, elution heptanes/AcOEt 98:2) and bulb-to-bulb distillation provided the end product.

II) General Procedure for the Reduction of the Ketone into the Alcohol

In a 100 ml flask, maintained under Ar atmosphere, were introduced 2 molar equivalents, with respect of the ketone, of $LiAlH_4$ in THF. Then the appropriate naphthalenone was added drop wise, at 0° C. After completion of the reaction, the mixture was stirred for 30 minutes at room temperature. Afterwards the reaction mixture was hydrolyzed with a stoechiometric amount of aqueous NaOH and the organic layer was dried over $Na_2SO_4$. Evaporation of the solvents and bulb-to-bulb distillation provided the end product.

III) General Procedure for the Hydrogenation of the Naphthalenone into the Perhydro Naphthalenone In a 100 ml flask were introduced the appropriate naphthalenone, ethyl acetate or cyclohexane and 5% Pd/C. The mixture was thus stirred under $H_2$, at room temperature, until consumption of the theoretical amount of hydrogen. Afterwards, the reaction mixture was filtered over Nylon 6/6. Evaporation of the solvents and bulb-to-bulb distillation provided the end product.

Preparation of 4,4,6,8a-tetramethyloctahydro-1(2H)-naphthalenone

The title compound was prepared according to general procedure III, with the following quantities of reagents: naphthalenone from example 1 (3.10 g; 0.015 mol) 5% Pd—C (0.3 g), ethyl acetate (30 ml)

3.12 g of a colorless liquid were obtained as a 45:22:27 mixture of isomers (regio- and stereo) (98% pure; 0.0147 mol; 98%). 4 diastereoisomers are present but not completely resolved on GC.

B.P.=87° C./0.013 mbar)

$^{1}$H-NMR: 2.72-2.62 (m, 1H); 2.30-2.08 (m, 2H); 2.40-1.40 (m, 6H); 1.38-1.10 (m, 9H); 1.05-0.82 (m, 6H).

Preparation of (4aRS,8aSR)-2-ethyl-4,4-dimethyl-3,4,4a,5,8,8a-hexahydronaphthalen-1(2H)-one The title compound was prepared according to general procedure I, with the following quantities of reagents:

6-Ethyl-4,4-dimethyl-2-cyclohexen-1-one (13.1 g; 0.086 mol), obtained according the method described for 6-methyl-4,4-dimethyl-2-cyclohexen-1-one (K. L. Cook, et al. in J. Chem. Soc., Perkin Transactions 1, 1973, 529)

1,3-Butadiene (9.31 g; 0.172 mol)

1 molar $AlEtCl_2$ in n-hexanes (43 ml; 0.043 mol), Dichloromethane (150 ml). 9.76 g of the desired product were obtained as a colorless liquid (93% pure, 0.044 mol; 51%).

BP.=90° C./0.012 mbar $^{13}$C-NMR: 212.53 (s); 125.03 (d); 124.48 (d); 47.44 (d); 46.75 (d); 43.96 (d); 42.91 (t); 33.31 (s); 27.89 (q); 27.48 (q); 24.40 (t); 24.25 (t); 22.07 (t); 11.72 (q).

$^{1}$H-NMR: 5.70-5.53 (m, 2H); 3.05 (m, 1H); 3.58-2.50 (m, 1H); 2.32-2.23 (m, 1H); 2.10-1.53 (m, 8H); 1.37 (s, 3H); 0.97 (s, 3H); 0.87 (t, J=7 Hz, 3H).

Preparation of (4aRS,8aSR)-2-ethyl-4,4-dimethyloctahydronaphthalen-1(2H)-one

The title compound was prepared according to general procedure III, with the following quantities of reagents:

(4aRS,8aSR)-2-ethyl-4,4-dimethyl-3,4,4a,5,8,8a-hexahydronaphthalen-1(2H)-one (2.4 g; 0.011 mol) herein above Pd—C (0.2 g), cyclohexane (15 ml)

2.25 g of desired product were obtained as a colorless liquid (0.0108 mol; 98%).

B.P.=90° C./0.015 mbar $^{13}$C-NMR: 213.67 (s); 51.12 (d); 47.45 (d); 45.71 (d); 41.68 (t); 33.42 (s); 28.33 (q); 27.63 (q); 26.74 (t); 25.82 (t); 25.34 (t); 21.98 (t); 11.72 (q).

$^{1}$H-NMR: 2.82 (m, 1H); 2.37-2.17 (m, 2H); 1.85-1.40 (m, 8H); 1.30 (s, 3H); 1.20-0.75 (m, 4H); 0.95 (s, 3H); 0.89 (t, J=7 Hz, 3H).

Preparation of (1RS,2RS,4aSR,8aSR)-2-ethyl-4,4-dimethyl-1,2,3,4,4a,5,8,8a-octahydronaphthalen-1-ol The title compound was prepared according to general procedure II, with the following quantities of reagents:

(4aRS,8aSR)-2-ethyl-4,4-dimethyl-3,4,4a,5,8,8a-hexahydronaphthalen-1(2H)-one (2.6 g; 0.0126 mol) herein above $LiAlH_4$ (0.3 g, 0.008 mol), THF (25 ml)

2.63 g of desired product were obtained (0.0126 mol, 100%) as mixture of diastereoisomers.

The major diastereoisomer was further purified by column chromatography on silica gel (eluent: heptanes/ethyl acetate 98:2) followed by bulb-to-bulb distillation to give 1.25 g of 100% pure compound (0.006 mol; 48%) as a colorless liquid.

B.P.=130° C./0.05 mbar)

$^{13}$C-NMR: 126.38 (d); 125.33 (d); 80.84 (d); 44.97 (t); 44.38 (d); 40.78 (d); 40.19 (d); 32.61 (s); 30.88 (t); 29.96 (q); 25.75 (t); 24.89 (t); 20.88 (q); 10.75 (q).

$^{1}$H-NMR: 5.67 (m, 2H); 2.83 (t, J=9.3 Hz, 1H); 2.55 (m, 1H); 2.07 (m, 1H); 1.85-1.67 (m, 3H); 1.58 (s, 1H); 1.52-1.36 (m, 3H); 1.22-1.03 (m, 2H); 0.90 (s, 3H); 0.89 (t, J=7 Hz, 3H); 0.85 (s, 3H).

Preparation of 8a-ethyl-4,4,6-trimethyl-3,4,4a,5,8,8a-hexahydronaphthalen-1(2H)-one The title compound was prepared according to general procedure I, with the following quantities of reagents:

2-ethyl-4,4-dimethyl-2-cyclohexen-1-one (CAS #69700-03-4; 15 g, 0.098 mol) Isoprene (13.29 g; 0.195 mol)

1 molar $AlEtCl_2$ in n-hexanes (19.5 ml; 0.0195 mol), dichloromethane (200 ml) 10.96 g of a 43:57 mixture of regioisomers were obtained as a colorless liquid (0.05 mol, 51%).

B.P.=105° C./0.015 mbar $^{13}$C-NMR: 215.79 (s); 215.52 (s); 132.52 (s); 130.38 (s); 119.81 (d); 117.88 (d); 50.94 (s); 49.93 (s); 42.37 (d); 41.62 (d); 39.32 (t); 38.26 (t); 35.57 (t); 34.25 (t); 33.41 (s); 33.15 (s); 32.30 (q); 32.25 (q); 28.18 (t); 27.87 (t); 27.57 (t); 23.56 (q); 23.50 (q); 23.02 (t); 21.85 (q); 21.82 (q); 9.27 (q); 9.23 (q).

$^{1}$H-NMR: 5.40-5.25 (m, 1H); 2.72-2.62 (m, 1H); 2.32-1.40 (m, 13H); 1.00 (m, 6H); 0.80 (m, 3H).

Preparation of (4aRS,8aSR)-2,4,4-trimethyl-3,4,4a,5,8,8a-hexahydronaphthalen-1(2H)-one The title compound was prepared according to general procedure I, with the following quantities of reagents:

4,4,6-trimethyl-2-cyclohexen-1-one (CAS #13395-73-8; 80% chemically pure; 32.78 g; 0.19 mol)

1,3-Butadiene (41.9 g; 0.76 mol)

1 molar $AlEtCl_2$ in n-hexanes (47.4 ml; 0.0474 mol), dichloromethane (300 ml)

A 60:40 mixture of diastereoisomers was obtained. The diastereoisomers were separated by column chromatography on silica gel (eluent: heptanes-ethyl acetate 25:1) and further purified by bulb-to-bulb distillation. 11.06 g of the title compound (0.058 mol, 30%) were obtained as colorless liquids.

B.P.=65° C./0.001 mbar)

$^{13}$C-NMR: 213.48 (s); 125.39 (d); 125.34 (d); 51.13 (t); 48.17 (d); 45.29 (d); 40.82 (d); 33.14 (s); 28.95 (q); 26.91 (t); 25.30 (t); 20.41 (q); 14.60 (q).

$^{1}$H-NMR: 5.70-5.60 (m, 2H); 2.65-2.55 (m, 1H); 2.37-1.96 (m, 5H); 1.75 (m, 1H); 1.56 (m, 1H); 1.45-1.35 (m, 1H); 1.13 (s, 3H); 1.01 (d, J=7 Hz, 3H); 0.98 (s, 3H).

Preparation of (2RS,4aSR,8aSR)-2,4,4-trimethyloctahydronaphthalen-1(2H)-one

The title compound was prepared according to general procedure III, with the following quantities of reagents:

(4aRS,8aSR)-2,4,4-trimethyl-3,4,4a,5,8,8a-hexahydronaphthalen-1(2H)-one (3.75 g, 0.0195 mol) herein above 5% Pd—C (0.15 g), cyclohexane (20 ml).

3.73 g of the desired product were obtained as a colorless liquid (0.0192 mol, 98%).

B.P.=50° C./0.001 mbar $^{13}$C-NMR: 214.28 (s); 53.24 (d); 51.76 (t); 49.45 (d); 40.96 (d); 33.44 (s); 28.83 (q); 27.93 (t); 26.14 (t); 25.93 (t); 25.38 (t); 20.38 (q); 14.50 (q).

$^{1}$H-NMR: 2.54 (m, 1H); 2.08 (m, 1H); 1.96 (m, 1H); 1.80-1.68 (m, 4H); 1.38-1.07 (m, 6H); 1.11 (s, 3H); 0.97 (d, J=7 Hz, 3H); 0.94 (s, 3H).

Preparation of a mixture of 4,4,6-trimethyl-3,4,4a,5,8,8a-hexahydro-1(2H)-naphthalenone and 3,4,4a,5,8,8a-hexahydro-4,4,6(7)-trimethyl-1(2H)-naphthalenone Addition drop wise of Tin(IV)chloride (86 ml, 0.735 mol) to a stirred solution of 4,4-dimethyl-cyclohexenone (60 g, 0.483 mol) in acetonitrile (200 ml) under $N_2$ over a period of 45 minutes. The temperature was always kept below 10° by means of an ice-water bath. The reaction mixture then allowed reaching 20° over 30 minutes, whereby a coloration to pale orange accompanied by a fine precipitation was observed. This slurry was then re-cooled to 0°, prior a quick drop wise addition of isoprene (100 g, 1.47 mol) over a period of 30 minutes. A slight exothermic reaction (+5°) can be observed. This mixture further stirred for 2 days at room temperature prior heating at reflux)(~60° for another 24 hours. The reaction mixture was then cooled to room temperature and subjected to the following work up: poured into icy water (500 ml) and extracted into ether (2×400 ml). The combined organic layer was washed with aqueous 5% NaCl (3×300 ml), aqueous saturated $NaHCO_3$ (1×300 ml) and finally with another portion of saturated aqueous NaCl (300 ml). Dried over sodium sulfate, filtered and concentrated to afford 71.5 g orange-brown oil. This rather complex mixture was then subjected to fractional distillation. The fraction (3.1 g), which was distilled at 69-72°/0.8 mbar, contains a 1/1-mixture of the targeted material. The yield considering unreacted starting material is around 14%.

$^{13}$C-NMR: 212.6 (s), 212.6 (s), 132.5 (s), 132.4 (s), 119.5 (d), 119.4 (d), 47.6 (d), 47.2 (d), 45.8 (d), 45.3 (d), 41.4 (t), 41.4 (t), 38.3 (t), 38.3 (t), 32.6 (s), 32.5 (s), 31.8 (t), 30.1 (t), 29.0 (q), 29.0 (q), 27.0 (t), 25.5 (t), 23.4 (q), 23.3 (q), 19.4 (q), 19.3 (q).

Example 3

Preparation of a Perfuming Composition

A perfuming composition for powder detergent was prepared by admixing the following ingredients:

| Ingredient | Parts by weight |
|---|---|
| Hexyl acetate | 150 |
| Geranyl acetate | 200 |
| Styrallyl acetate | 50 |
| 10%* Methyl anthranilate | 40 |
| 10%* Ethyl 2-methyl-pentanoate | 60 |
| Gamma undecalactone | 100 |
| 10%* Ethyle butyrate | 40 |
| Calone ®[1] | 50 |
| Cinnamon essential oil | 10 |
| Lemon essential oil | 250 |
| Citronellol | 300 |
| Damascone delta | 20 |
| Ethyl linalol | 600 |
| Ethylpraline | 10 |
| 3-(4-Methoxyphenyl)-2-methylpropanal | 100 |
| 70%* Galaxolide ®[2] | 2000 |
| Hedione ®[3] HC | 1000 |
| 3-(1,3-Benzodioxol-5-yl)-2-methylpropanal | 300 |
| (E)-3-Methyl-4-(2,6,6-trimethyl-2-cyclohexen-1-yl)-3-buten-2-one | 300 |
| Carbonate de 3-hexenyl-methyle | 40 |
| Lilial ®[4] | 1000 |
| 6,6-Dimethoxy-2,5,5-trimethyl-2-hexene | 200 |
| 10%* Rose oxide | 60 |
| Phenethylol | 200 |
| Orange essential oil | 450 |
| (Z)-3-Hexen-1-ol salicylate | 600 |
| 3-Methyl-5-(2,2,3-trimethyl-3-cyclopenten-1-yl)-2-pentanol | 100 |
| Vanilline | 10 |
| Beta ionone | 200 |
| 2,4-Dimethyl-3-cyclohexene-1-carbaldehyde | 60 |
| | 8500 |

*in dipropyleneglycol

[1] 7-methyl-2H,4H-1,5-benzodioxepin-3-one; origin: Firmenich SA, Geneva, Switzerland

[2] 1,3,4,6,7,8-hexahydro-4,6,6,7,8,8-hexamethyl-cyclopenta-g-2-benzopyrane; origin: International Flavors & Fragrances, USA

[3] methyl cis-dihydrojasmonate; origin: Firmenich SA, Geneva, Switzerland

[4] 3-(4-tert-butylphenyl)-2-methylpropanal; origin: Givaudan SA, Vernier, Switzerland The addition of 1500 parts by weight of a mixture 70/30 w/w of (4aRS,8aRS)-4,4,6,8a-tetramethyl-3,4,4a,5,8,8a-hexahydronaphthalen-1(2H)-one and (4aRS,8aRS)-4,4,7,8a-tetramethyl-3,4,4a,5,8,8a-hexahydronaphthalen-1(2H)-one (compounds as described in Example 1.a)) to the above-described composition imparted to the latter strong musky note and also a spicy peppery note.

The addition of 1500 parts by weight of a 4,6,8a-trimethyl-3,4,4a,5,8,8a-hexahydro-1(2H)-naphthalenone did not impart any musky or spicy note, but rather a cedar, ambery character.

Example 4

Preparation of a Perfuming Composition

A perfuming composition for a woman fine perfume was prepared by admixing the following ingredients:

| Ingredient | Parts by weight |
|---|---|
| Aldehyde C 11 lic | 150 |
| Aldehyde hexylcinnamic | 1500 |
| Citronellol | 500 |
| Citronellyl nitrile | 50 |
| Verdyl acetate | 600 |
| Verdyl propionate | 300 |
| Dihydromyrcenol | 1000 |
| Diphenyloxyde | 250 |
| Lavander essential oil | 100 |
| Lilial ®[1] | 600 |
| Hedione ®[2] | 600 |
| (1'R)-2-[2-(4'-methyl-3'-cyclohexen-1'-yl)propyl]cyclopentanone[3] | 50 |
| Phenethylol | 150 |
| Polysantol ®[4] | 100 |
| Hexyl salicylate | 400 |
| Undecavertol ®[5] | 50 |

-continued

| Ingredient | Parts by weight |
|---|---|
| Verdox ®[6] | 800 |
| Yara yara | 200 |
| 2,4-Dimethyl-3-cyclohexene-1-carbaldehyde | 100 |
| | 7500 |

[1]3-(4-tert-butylphenyl)-2-methylpropanal; origin: Givaudan SA, Vernier, Switzerland
[2]methyl dihydrojasmonate; origin: Firmenich SA, Geneva, Switzerland
[3]origin: Firmenich SA, Geneva, Switzerland
[4]3,3-dimethyl-5-(2,2,3-trimethyl-3-cyclopenten-1-yl)-4-penten-2-ol; origin: Firmenich SA, Geneva, Switzerland
[5]4-methyl-3-decen-5-ol; origin: Givaudan SA, Vernier, Switzerland
[6]2-tert-butyl-1-cyclohexyl acetate; origin: International Flavors & Fragrances, USA The addition of 2500 parts by weight of a mixture as described in Example 1.a) to the above-described composition imparted to the latter an interesting and new spicy note reminiscent of pepper and wasabi. The invention's compound provided also a strong musky and balsamic note.

The addition of 2500 parts by weight of a 4,6,8a-trimethyl-3,4,4a,5,8,8a-hexahydro-1(2H)-naphthalenone did not impart any musky or spicy note, but rather a earthy-patchouli character.

The invention claimed is:

1. A method to confer, enhance, improve or modify the odor properties of a perfuming composition or of a perfumed article, which method comprises adding to said composition or article an effective amount of a compound of formula

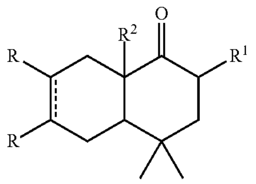

wherein:

the dotted line represents a single or double bond;

one R represents a hydrogen atom and the other R represents a methyl group;

$R^1$ represents a hydrogen atom, a methyl group or an ethyl group;

$R^2$ represents a hydrogen atom or a methyl or ethyl group; and the groups R, $R^1$ and $R^2$ have in total 1 to 4 carbon atoms.

2. The method according to claim 1, wherein one of said $R^2$ and $R^1$ represents a hydrogen atom and the other is not a hydrogen atom.

3. The method according to claim 1, wherein said compound is selected amongst (4aRS,8aRS)-4,4,6,8a-tetramethyl-3,4,4a,5,8,8a-hexahydronaphthalen-1(2H)-one or (4aRS,8aRS)-4,4,7,8a-tetramethyl-3,4,4a,5,8,8a-hexahydronaphthalen-1(2H)-one and mixtures thereof, 8a-ethyl-4,4,6-trimethyl-3,4,4a,5,8,8a-hexahydronaphthalen-1(2H)-one, dimethyloctahydronaphthalen-1(2H)-one or (4aRS,8aSR)-2-ethyl-4,4-dimethyl 3,4,4a,5,8,8a-hexahydronaphthalen-1(2H)-one.

4. The method according to claim 1, wherein said compound is selected amongst 4aRS,8aRS)-4,4,6,8a-tetramethyl-3,4,4a,5,8,8a-hexahydronaphthalen-1(2H)-one or (4aRS,8aRS)-4,4,7,8a-tetramethyl-3,4,4a,5,8,8a-hexahydronaphthalen-1(2H)-one and mixtures thereof.

5. The method of claim 1 wherein in the compound the groups R, $R^1$ and $R^2$ have in total 2 to 3 carbon atoms.

6. The method according to claim 1 wherein the compound is added in combination with at least one ingredient selected from the group consisting of a perfumery carrier and a perfumery base in order to provide thereto odor notes of the woody type together with balsamic/spicy and musky notes.

7. The method according to claim 1 wherein the compound is added to a perfuming composition comprising at least one ingredient selected from the group consisting of a perfumery carrier and a perfumery base; and optionally at least one perfumery adjuvant.

8. The method according to claim 1 wherein the compound is added to a perfuming consumer product that includes a perfumery consumer base.

9. The method according to claim 8, wherein the perfumery consumer base is a perfume, a fabric care product, a body-care product, an air care product or a home care product.

10. The method according to claim 8, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

11. A perfuming composition comprising i) at least one compound of the formula defined in claim 1 in combination with at least one ingredient selected from the group consisting of a perfumery carrier and a perfumery base which provides thereto odor notes of the woody type together with balsamic/spicy and musky notes;

ii) at least one ingredient selected from the group consisting of a perfumery carrier and a perfumery base; and iii) optionally at least one perfumery adjuvant.

12. The composition of claim 11 wherein in the compound the groups R, $R^1$ and $R^2$ have in total 2 to 3 carbon atoms.

13. A perfuming consumer product comprising:

i) at least one compound of the formula defined in claim 1 in combination with at least one ingredient selected from the group consisting of a perfumery carrier and a perfumery base which provides thereto odor notes of the woody type together with balsamic/spicy and musky notes; and ii) a perfumery consumer base.

14. The consumer product of claim 13 wherein in the compound the groups R, $R^1$ and $R^2$ have in total 2 to 3 carbon atoms.

15. The perfuming consumer product according to claim 13, wherein the perfumery consumer base is a perfume, a fabric care product, a body-care product, an air care product or a home care product.

16. The perfuming consumer product according to claim 13, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *